United States Patent [19]

Klemola et al.

[11] Patent Number: 4,847,422
[45] Date of Patent: Jul. 11, 1989

[54] METHOD FOR THE PRODUCTION OF VANILLIN

[75] Inventors: Aarno Klemola; Juhani Tuovinen, both of Valkeakoski, Finland

[73] Assignee: Yhtyneet Paperitehtaat Oy, Valkeakoski, Finland

[21] Appl. No.: 105,579

[22] Filed: Oct. 8, 1987

Related U.S. Application Data

[63] Continuation-in-part of Ser. No. 834,772, Feb. 28, 1986.

[30] Foreign Application Priority Data

Mar. 1, 1985 [FI] Finland ................................ 850858

[51] Int. Cl.⁴ ............................................. C07C 45/78
[52] U.S. Cl. .................................... 568/438; 568/426
[58] Field of Search .................................. 568/426, 438

[56] References Cited

U.S. PATENT DOCUMENTS

| | | | |
|---|---|---|---|
| 4,075,248 | 2/1978 | Marshall et al. | 568/438 |
| 4,198,432 | 4/1980 | Vitzhum et al. | 426/312 |
| 4,474,994 | 10/1984 | Makin | 568/438 |

FOREIGN PATENT DOCUMENTS

| | | | |
|---|---|---|---|
| 2578246 | 9/1986 | France | 568/438 |
| 318939 | 9/1929 | United Kingdom | 568/438 |
| 87/01695 | 3/1987 | World Int. Prop. O. | 568/438 |

OTHER PUBLICATIONS

McDonald et al., 098(22)181320 Chemabs Journal, vol. 98, 1983, "Chemicals from Forest Products by Supercritical Fluid Extraction".

Primary Examiner—Werren B. Lone
Attorney, Agent, or Firm—Cushman, Darby & Cushman

[57] ABSTRACT

The invention relates to a method for the production of vanillin in the form of a very pure product by oxidizing lignin contained in the wood pulping liquor. According to the invention the separation and purification of vanillin from the reaction mixture is carried out by means of an extraction at a supercritical pressure and temperature. Carbon dioxide, for instance, can be used as a extraction gas.

12 Claims, 1 Drawing Sheet

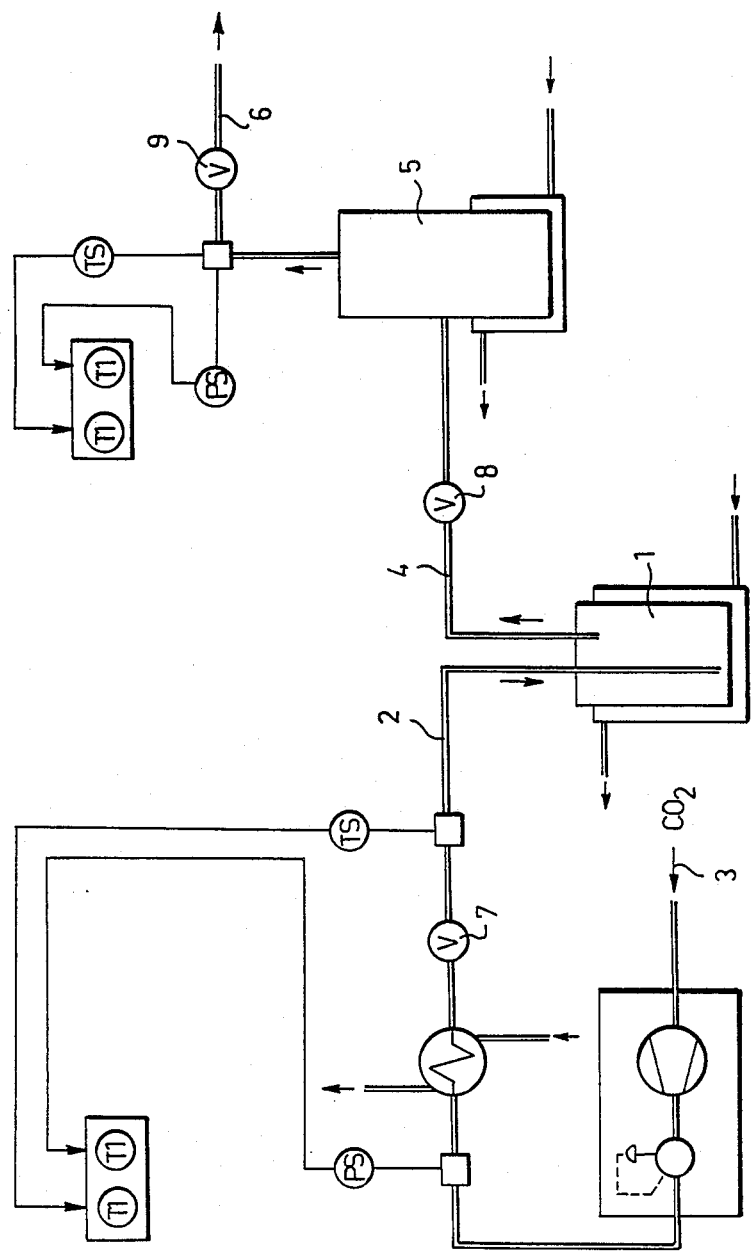

METHOD FOR THE PRODUCTION OF VANILLIN

This is a continuation-in-part of application Ser. No. 834,772 filed Feb. 28, 1986.

The invention relates to a method for the production of vanillin, by oxidizing in basic conditions waste liquor obtained from the production of wood pulp and then bringing the pH of the waste liquor to a value at which vanillin occurs mainly in the form of a phenol.

The invention is characterized by extracting the vanillin with supercritical carbon dioxide at a pressure from 75 to 400 bars and a temperature from 30° to 100° C. by passing a carbon dioxide flow through said oxidized waste liquor until an essential portion of the vanillin is dissolved in said carbon dioxide flow, from which it is separated by passing said gas flow into a receiver having pressure and temperature conditions favorable for the separation of vanillin.

Vanillin is commonly prepared by oxidizing waste liquor formed in the productions of pulp, more particularly, the lignin contained in said waste liquor, by means of an oxygen-containing gas using heavy metals or oxides thereof as a catalyst. The oxidation conditions being generally known, they are not discussed in this connection. The lignin available in the waste liquor of sulphite pulping processes is structurally more suitable for the formation of vanillin than the lignin obtained by sulphate of alkali pulping processes. For this reason, the waste liquors of sulphite processes are the most common starting materials in the industrial production of vanillin. Softwood is thereby used as wood raw material in the production of pulp, because the lignins contained in hardwood include not only so called quaiacyl units (4-hydroxy-3-methoxyphenyl-) but also syringyl units (4-hydroxy-3.5-dimethoxyphenyl-) which in the oxidation of vanillin produce syringaldehyde (4-hydroxy-3.5-dimethoxybenzaldehyde). This substance is difficult to separate from vanillin when pure vanillin is to be obtained.

It is common practice to separate vanillin from the oxidized waste liquor by extraction carried out either directly by means of an organic, partially water soluble solvent, e.g. Finnish Patent Specification No. 20,078 (1944), or after acidification by means of less polar organic solvents, e.g. Finnish Patent Specification No. 17,966 (1936). N-butanol in the first-mentioned and toluene in the latter alternative are typical examples of extraction solvents.

On industrial scale, several difficulties are involved in the extraction of vanillin from the oxidized wood pulping waste liquor by means of an organic solvent.

Solution volumes are large and solvents inflammable. The oxidized liquor contains surface-active agents, which easily leads to the formation of emulsions during the extraction and, consequently, to disturbances in the process. The oxidized liquor contains large quantities of other phenolic, lignin decomposition products similar to vanillin, which are extracted besides vanillin, whereby a multi-stage treatment is required for the separation of said substances from the vanillin when a pure quality of vanillin suitable for technical applications or foodstuffs is to be obtained.

The present invention for one thing provides considerable advantages in the extraction of vanillin from an oxidized liquor. It has been unexpectantly discovered that when vanillin is extracted from the oxidized waste liquor after the neutralization by means of overpressurized carbon dioxide, it can be quantitatively recovered under fully controllable extraction conditions. Besides, the purity degree of the extracted vanillin is high.

Supercritical extraction means a procedure wherein the extracting agent is, in the gaseous form, above the critical pressure and temperature thereof. Such extraction can be carried out by means of various agents, though carbon dioxide, the critical pressure of which is 73.8 bars and the critical temperature 31° C., has become most popular, being inert, nontoxic, uninflammable and easy to handle.

Supercritical extraction has already long been known even though it has been more extensively applied industrially only recently, e.g. for the separation of coffeine and spices. A summary of such industrial applications is to be found e.g. in the publications Process Engineering No. 6, 1983, p. 32–35 and German Chemical Engineering No. 6, 1984, p. 335–344.

Also the extraction of vanillin and other phenolic substances by supercritical gases is known from the literature. Calinili and Olcay (Holzforsch. 32 (1978):1, 7–10) extracted spruce wood under supercritical conditions by acetone, tetrahydrofurane, and toluene, whereby the extracts obtained contained small quantities of phenols (3.0 to 5.5 per cent), among which there was vanillin (0.1 to 0.15 per cent based on the wood content). McDonald et al. (Fluid Phase Equil. 10 (1983): 2–3, 337–344) extracted North American red cedar by supercritical acetone and supercritical methanol and identified from the extract substituted guaiacols and levolucosanes, the total amount of which was below 3.7 per cent based on the wood content.

Now it has been unexpectedly discovered that it is possible to extract vanillin from a quantitatively oxidized sulphite waste liquor by means of supercritical carbon dioxide. Water is poorly soluble in supercritical carbon dioxide and does not impede the process. The high alkalinity of the oxidized liquor retains the vanillin contained therein as a sodium salt and the extraction of vanillin is not accelerated until the pH is reduced within the neutral range. The carbon dioxide reduces the pH of the oxidized waste liquor; instead of a pure supercritical carbon dioxide the neutralization, however, can be more economically effected by means of a flue gas. Naturally, the neutralization can also be carried out by means of mineral acids.

As a unit operation in a vanillin production process, a supercritical carbon dioxide extraction may replace extraction with an organic solvent as well as re-extraction into water. Handling of large amounts of inflammable and ecologically disadvantageous solvents can be avoided through extraction by supercritical carbon dioxide; however, this is not the only advantage. Another equally important advantage is that the purity degree of vanillin extracted by supercritical carbon dioxide is enormously higher than that of so called raw vanillin, i.e. vanillin extracted by organic solvents. With a supercritical carbon dioxide extraction, the purity degree of the raw vanillin is in the range of 90 per cent while it is merely in the range of 60 per cent after a solvent extraction (Example 2).

The purification of raw vanillin is a multi-stage process if a commercially useful final product is to be obtained. Among the purification steps, which have been described in e.g. Kirk-Othmer; Encyclopedia of Chemical Technology, 3rd Ed., Vol. 23, p. 700–710, it should be mentioned removal of non-aldehydic impurities from the bisulphite complex of vanillin, vacuum distallation of vanillin and crystallization. These purification steps provide a pure quality of raw vanillin suitable for technical applications (vanillin concentration more than 97 per cent) and, further, a quality of a still greater purity suitable for foodstuffs (vanillin concentration 99.8 per cent).

The impurities of vanillin mainly consist either of vanillin related substances or other phenolic, lignin decomposition products having a higher molecular weight. A great number of the former has been identified; besides those analyzed in the examples, there are such common impurities of vanillin as e.g. o-vanillin, 5-formyl vanillin, vanillin acid and dehydrodivanillin. The most important component of this kind of substances is usually acetoguaiacol which during the oxidation step is often produced in the amount of about 10 percent based on the amount of vanillin.

Another group of impurities consists of partially desulphonated phenolic substances formed in the oxidation of lignosulphonates and having a molecular weight 2 to 10 times the molecular size of vanillin. These substances are not identified in vanillin analyses as they are not sufficiently volatile to be analyzed by means of gas chromatography. The amounts thereof in the raw vanillin may be remarkable, up to 40 per cent, depending on the solvent extraction of vanillin.

These lignin decomposition products have proved harmful in the purification of vanillin. They easily form tars when the bisulphite complex of vanillin is being formed or decomposed, which easily leads to disturbances in the process. The tars reduce the vanillin yield by dissolving the same and above all by binding vanillin to themselves in the vacuum distillation thereof.

Now it has been discovered that when vanillin is extracted from the oxidation solution thereof by supercritical carbon dioxide, these "oligomeric", lignin decomposition products are nearly completely retained in the oxidation solution. In fact, this is also to be expected on account of the low vapour pressure thereof and, presumably, for their poor solubility in carbon dioxide. Even though the vanillin related substances, which contain one aromatic ring, to a great extent follow vanillin in the supercritical extraction, the vanillin purification is thereby substantially easier than after a solvent extraction. Vanillin losses in the purification steps are thereby considerably decreased. It is also possible to reduce the number of the purification steps. The purity degree required of a vanillin suitable for technical applications can be obtained already with a single crystallization from water (Example 5). As a whole, the notably higher degree of purity of the raw product in the carbon dioxide extract provides substantial economical advantages in the purification thereof into a commercially useful product as compared with the purification of a raw vanillin extracted by an organic solvent.

The purity degree of the carbon dioxide extract is within the same range irrespective of whether the extraction is carried out from an oxidized waste liquor or from a vanillin product separated therefrom by an organic solvent (Examples 2, 3 and 6). It is to be emphasized that the present method is based on the extraction of vanillin in particular. A recent patent (U.S. Pat. No. 4,474,994; 1984) discloses a purification of raw vanillin (extracted by an organic solvent) by extraction therefrom impurities, including oligomeric ones, by supercritical carbon dioxide, whereby there remains a vanillin of a greater purity. As disclosed below in Example 1 according to the present invention, vanillin is rather easily soluble in supercritical carbon dioxide.

A further advantage of a direct extraction of vanillin from an oxidized liquor is that it enables the process to be operated continuously by passing the carbon dioxide and waste liquor flows upstreams.

The process differs clearly from that disclosed in the U.S. Pat. No. 4,474,994. Instead of weight ratio from 1:1 to 100:1 of $CO_2$ to vanillin as given in the U.S. Pat. No. 4,474,994, we have found out that with a weight ratio from 200:1 to 800:1 vanillin can completely be extracted from dilute water solutions as well as from concentrates. On the other hand, tar residues like oligomeric lignin degradation products remain unextracted even with such $CO_2$: vanillin ratios. This is indicated by g.l.c. data, where the tar components not eluted are calculated as the difference between the sample amount and those eluted, or by DSC. However, the most sensitive indicator of vanillin purity is its melting point, which is depressed even by small amounts of impurities.

The desired product can to a certain degree be separated selectively by means of supercritical extraction. This is apparent from Example 1, wherein the pressure and the density of the extracting agent, i.e. carbon dioxide, are given under the conditions in which vanillin and certain common impurities thereof are dissolved in carbon dioxide. Increase in the polarity decreases solubility (p-hydroxybenzaldehyde), whereas a high vapour pressure (guaiacol) increases it. As stated above, these matters contribute to the liberation of vanillin from a plurality of lignin decomposition products in supercritical extraction.

The same laws apply to the separation of vanillin from a supercritical gas flow. Compounds having the lowest solubility in carbon dioxide are most easily separated therefrom by suitably varying the pressure and/or the temperature. By systematically calculating the pressures in extraction vessels arranged in a series, for instance, it is possible to fraction out compounds from a supercritical gas flow flowing through the system, thus increasing the purity degree of the main component, i.e. vanillin in this particular case.

The invention will be in the attached drawing and the following examples. In the drawing an extraction autoclave 1 is connected by means of a pipe 2 with a carbon dioxide source 3. The outlet of the autoclave is connected by means of a pipe 4 with a separation autoclave 5 provided with an outlet pipe 6. The reference numerals 7, 8 and 9 indicate flow control valves.

EXAMPLE 1

Approximately 100 milligrams of vanillin and related substances were introduced into a chamber, the temperature of which was raised to 60° C. and which was pressurized by means of carbon dioxide. By means of a sight glass, it was controlled when said substances were dissolved in carbon dioxide as the pressure thereof was increased. The process was seen clearly and sharply.

| Amount (g) | Pressure (bar) | Temperature (°C.) | Density of carbon dioxide (g/dm3) |
|---|---|---|---|
| Vanillin, 0.1066 | 220 | 62 | 735 |
| Acetoguaiacol, 0.1066 | 350 | 61 | 860 |
| Parahydroxybenzaldehyde, 0.0148 | 380 | 60 | 876 (incompletely solved) |
| Guaiacol, 0.1047 | 120 | 60 | 368 |

EXAMPLE 2

A waste liquor obtained from an industrial scale semi-alkaline sulphite pulping process was oxidized by means of air in the presence of a copper catalyst for the production of vanillin. The oxidized liquor was neutralized and extracted with toluene for determining the vanillin yield and impurities by means of gas chromatography. The vanillin yield in the oxidation was 9.33% calculated on the lignin contained in the waste liquor.

In an apparatus according to the drawing, an amount of 50 ml of the neutralized waste liquor was extracted by means of carbon dioxide. The extraction pressure was 150 bars and the temperature 60° C. Substances dissolved in the carbon dioxide were separated when the mixture was passed into an extraction vessel having standard pressure and a temperature of 25° C. The composition of the white extract was determined by means of gas chromatography.

|  | Oxidized waste liquor | Carbon dioxide-extract |
|---|---|---|
| Vanillin | 56.2% | 88.0% |
| Acetoguaiacol | 4.5% | 5.0% |
| Parahydroxybenzaldehyde (PHB) | 1.3% | 1.0% |
| Guaiacol | 1.8% | 1.9% |
| Syringaldehyde | 0.3% | 0.2% |
| Other peaks in the chromatogram | 5.9% | 2.6% |
| Not eluted in g.l.c. | 29.9% | 1.3% |
|  | 100.00% | 100.00% |

The vanillin yield in the carbon dioxide extraction was 96.8% with a total flow of 700 pts of $CO_2$ to one part of vanillin (W/W).

DSC-analysis of the extract gave a purity of 89.3 mole-% for vanillin. The melting point of the extract was 78.5° C.

EXAMPLE 3

An oxidized and neutralized waste liquor according to Example 2 was extracted by means of carbon dioxide at a pressure of 230 bars and a temperature of 60° C. The yield was gathered as in Example 2 and was crystallized twice from water, whereby the melting point was 81.5° C. The composition of the extract before and after recrystallization was:

| Vanillin | 91.0% |
|---|---|
| Acetoguaiacol | 5.0% |
| PHB | 0.7% |
| Guaiacol | 2.1% |
| Syringaldehyde | 0.2% |
| Other substances | 1.0% |
|  | 100.00% |

The vanillin yield in the extraction was 98.0% using a total flow of 800 pts of $CO_2$ to one part of vanillin (W/W).

EXAMPLE 4

An oxidized and neutralized water liquor according to Example 2 was extracted by means of carbon dioxide at a pressure of 350 bars and a temperature of 60° C. The yield was gathered as in Example 2, the composition thereof being:

| Vanillin | 90.0% |
|---|---|
| Acetoguaiacol | 6.0% |
| PHB | 0.7% |
| Guaiacol | 2.0% |
| Syringaldehyde | 0.2% |
| Other substances | 1.1% |
|  | 100.00% |

The vanillin yield in the extraction was 98.0%.

EXAMPLE 5

An oxidized and neutralized waste liquor according to Example 2 was extracted by means of carbon dioxide at a pressure of 125 bars and a temperature of 60° C. The flow of $CO_2$ was about 600 pts to one part of vanillin in the waste liquor. The yield was gathered into an autoclave, wherein the pressure was 50 bars and the temperature 30° C. The extract was crystallized twice from water, whereby the melting points were 81.0° C. and 81.5° C., respectively. The analysis of the extract before and after the crystallization:

|  | Crystallized extract | Twice-crystallized extract |
|---|---|---|
| Vanillin | 98.32% | 99.58% |
| Acetoguaiacol | 1.24% | 0.25% |
| PHB | 0.11% | 0.01% |
| Guaiacol | 0.10% | 0.06% |
| Syringaldehyde | 0.05% | 0.02% |
| Other substances | 0.18% | 0.08% |
| Purity by DSC (mole %) | 98.45.% | 99.96% |

EXAMPLE 6

An oxidized waste liquor from a semi-alkaline sulphite pulping process according to Example 2 was extracted after the neutralization by means of toluene with a continuously operated device. The toluene liquor was evaporated and the extract was analyzed by means of gas chromatography. Crystallization of the reddish brown extract was not successful, for it was not possible to separate the small quantity of white crystals from the tar-like sludge. When the toluene extract was treated in the extraction chamber by means of carbon dioxide at a pressure of 125 bars and a temperature of 60° C. and the gas flow (600 pts to one part of sample) was subsequently passed into an autoclave, wherein the pressure was dropped to 10 bars and the temperature to 30° C., a yellowish mass was separated from the gas flow. It was easily crystallized from water in the form of an almost white crystal sludge. The results of the analysis at different stages were as follows:

|  | Toluene extract | $CO_2$-extract of the foregoing | Crystallized $CO_2$-extract |
|---|---|---|---|
| Vanillin | 72.95% | 86.90% | 97.54% |
| Acetoguaiacol | 5.20% | 6.96% | 2.19% |
| PHB | 0.77% | 1.02% | 0.09% |
| Guaiacol | 0.83% | 1.96% | 0.07% |
| Syringaldehyde | 0.66% | 0.72% | 0.01% |
| Other peaks in the chromatogram | 1.38% | 0.81% | 0.10% |
| Not eluted in g.l.c. | 18.21% | 1.63% | — |
|  | 100.00% | 100.00% | 100.00% |

The melting point of the $CO_2$-extract once crystallized from water was 81.0° C., and the purity of vanillin was 96.24 mole-% as indicated by DSC-analysis.

We claim:

1. A method for the production of vanillin by oxidizing in air, and under basic conditions, waste liquor obtained from a wood pulping process and then bringing the pH of said waste liquor to a value at which the vanillin occurs mainly in the form of a phenol, characterized by extracting the vanillin with supercritical carbon dioxide at a pressure of from 75 to 400 bars and a temperature of from 30° to 100° C. by passing a carbon dioxide flow at a ratio of 400 to 1000 parts $CO_2$ to one part of vanillin, through said oxidized waste, and separating the vanillin dissolved in the gas flow by passing said gas flow into a receiver having pressure and temperature conditions favorable for the separation of vanillin.

2. The method according to claim 1, characterized by separating the vanillin from the gas flow at a pressure from 0 to 100 bars and at a temperature from 5° to 50° C.

3. The method according to claim 2, wherein a gas flow pressure of from 0 to 60 bars is used at a temperature of 25° to 40° C.

4. The method according to claim 1, characterized by decreasing gradually the pressure and temperature of the vanillin-containing gas flow in the receivers arranged in a series in such a manner that substances having a low solubility in carbon dioxide are first fractioned out of the gas flow, substances having a higher solubility than vanillin being fractioned after vanillin by decreasing gradually the pressure and/or temperature of the gas flow, and by recycling the by-fractions back to the beginning of the extraction and separation process.

5. The method according to claim 1, characterized in that the starting material is a pre-fractioned vanillin product.

6. The method according to claim 1, characterized in that the carbon dioxide gas contains 0.1 to 10 percent by weight of a polar, organic substance, a so called entrainer.

7. A method for the production of vanillin comprising the steps of:
   (a) oxidizing in air, and under basic conditions, waste liquor from a wood pulping process;
   (b) adjusting the pH of said waste liquor to a value at which the vanillin occurs mainly in the form of a phenol;
   (c) dissolving an essential portion of the vanillin in a flowing stream of supercritical carbon dioxide at a pressure from 75 to 400 bars and a temperature from 30° to 100° C. by passing said stream through said waste liquor; and
   (d) separating said vanillin from said stream by passing the stream into a receiver having pressure and temperature conditions favorable for the separation of vanillin.

8. The method of claim 7 wherein said separating step occurs at a pressure of from 0–100 bars and a temperature of from 5°–50° C.

9. The method of claim 8 wherein said separating step occurs at a pressure of from 0–60 bars and a temperature of from 25°–40° C.

10. The method of claim 7 wherein the starting material is a pre-fractional vanillin product.

11. The method of claim 7 wherein the carbon dioxide gas contains 0.1 to 10% by weight of a polar, organic substance.

12. The method of claim 7 wherein the separating step comprises decreasing gradually the pressure and temperature of the vanillin-containing gas flow in receivers arranged in a series in such a manner that substances having a low solubility in carbon dioxide are first fractioned out of the gas flow, substances having a higher solubility than vanillin being fractioned after vanillin by decreasing gradually the pressure and/or temperature of the gas flow, and by recycling the by-fractions back to the beginning of the extraction and separation process.

* * * * *